United States Patent
Nakamichi et al.

Patent Number: 5,456,923
Date of Patent: Oct. 10, 1995

[54] METHOD OF MANUFACTURING SOLID DISPERSION

[75] Inventors: Kouichi Nakamichi, Shiga; Shogo Izumi, Kyoto; Hiroyuki Yasuura, Shiga, all of Japan

[73] Assignee: Nippon Shinyaku Comapny, Limited, Japan

[21] Appl. No.: 129,133

[22] PCT Filed: Dec. 23, 1993

[86] PCT No.: PCT/JP92/00470

§ 371 Date: Nov. 15, 1993

§ 102(e) Date: Nov. 15, 1993

[87] PCT Pub. No.: WO92/18106

PCT Pub. Date: Oct. 29, 1992

[30] Foreign Application Priority Data

Apr. 16, 1991 [JP] Japan ................... 3-112554

[51] Int. Cl.⁶ ................ A61K 9/10; A61K 9/14
[52] U.S. Cl. ............ 424/489; 424/452; 424/455; 424/465; 514/772.2; 514/772.3; 514/774; 514/778; 514/779; 514/781; 514/937
[58] Field of Search ............... 424/464, 465, 424/452, 455, 489; 514/772.1, 772.3, 773, 777

[56] References Cited

U.S. PATENT DOCUMENTS 4,801,460  1/1989  Goertz et al. ................ 424/465
4,880,585  11/1989  Klimesch et al. ............ 264/141
4,992,100  2/1991  Koepff et al. ................ 106/125
5,073,379  12/1991  Klimesch et al. ............ 424/467
5,102,668  4/1992  Eichel et al. ................. 424/490

FOREIGN PATENT DOCUMENTS 8976091  6/1992  Australia .
0368247  11/1989  European Pat. Off. .
0375063  12/1989  European Pat. Off. .
1504553  11/1975  United Kingdom .

OTHER PUBLICATIONS

English language Abstract JP-A-62040277. Feb. 1987.
English language Abstract JP-A-58109411. Jun. 1983.

Primary Examiner—Thurman K. Page
Assistant Examiner—James M. Spear
Attorney, Agent, or Firm—Rosenman & Colin

[57] ABSTRACT

The object of this invention is to provide a process for producing a solid dispersion, which has overcome the disadvantages of the conventional production technology for solid dispersions. The invention comprises employing a twin-screw extruder in the production of a solid dispersion. In accordance with the invention, a solid dispersion can be expediently produced without heating a drug and a polymer to or beyond their melting points and without using an organic solvent for dissolving both components and the resulting solid dispersion has excellent performance characteristics.

12 Claims, 7 Drawing Sheets

METHOD OF MANUFACTURING SOLID DISPERSION

This application is a 371 of PCT/JP92/00470 filed Apr. 14, 1992.

TECHNICAL FIELD

The present invention relates to a process for producing a solid dispersion. More particularly, the invention relates to a process for producing a solid dispersion utilizing a twin-screw extruder, which finds application chiefly in the field of pharmaceutical manufacture.

The term 'solid dispersion' is used herein to mean a drug-containing pharmaceutical bulk substance comprising the drug dissolved or dispersed in a polymer.

BACKGROUND ART

Solid dispersions are of use for an enhanced solubility of drugs or for controlling the rate of release of a drug from a dosage form or improving the bioavailability of drugs, thus being of significant commercial value.

The conventional technology for the production of a solid dispersion includes a fusion process which is characterized by melting a drug and a polymer together at elevated temperature and, then, cooling the melt to solidify, a solvent process which is characterized by dissolving a drug and a polymer in an appropriate solvent and, then, removing the solvent, and a fusion-solvent process which has the characteristics of said processes.

However, the fusion process has the disadvantage that it cannot be applied to a drug or polymer which is, or is likely to be, thermally degraded.

The solvent process is free from the above-mentioned disadvantage of the fusion process but because it employs an organic solvent such as an alcohol or a chlorine-containing solvent, this process has the following disadvantages.

(1) When an alcohol is used as the solvent, strict measures must be provided for the prevention of an explosion hazard during production.

(2) Since organic solvents have fairly high affinities for the polymer, they cannot be easily removed from the product solid dispersions.

(3) Removal of the solvent necessarily results in its diffusion into the atmosphere to cause an atmospheric pollution.

(4) After removal of the solvent, the solid dispersion adhering intimately to the vessel wall cannot be easily withdrawn from the vessel.

DISCLOSURE OF INVENTION

The object of the present invention is to establish an improved process for producing a solid dispersion which has overcome the above-mentioned inherent disadvantages of the fusion and solvent processes.

The substantive feature of the present invention resides in the processing of the drug, polymer and other components for a solid dispersion by utilizing a twin-screw extruder.

The present invention is now described in detail.

The twin-screw extruder is a forward-discharge extruder-granulator characterized by the use of a couple of screws, which differentiate the machine from the so-called single-screw extruder. To be more specific, the twin-screw extruder comprises a metering feeder unit, a barrel (cylinder), screws, paddle means, screw shafts, barrel heater-cooler means, exit dies (cooling die, heating die, molding die) and extrudate cutter and provides for a free variation of compounding pressure and molding temperature through a choice of screw geometry, rotational speed, and screw elements to be mounted on the screw shafts. Furthermore, if necessary, the barrel can be used in a variety of combinations of length and type according to the intended use and its temperature can also be controlled as desired.

Thus, the twin-screw extruder processes the feed with two screws and provides for change of the combination of axial screw elements so that it has many definite advantages over the single-screw extruder, viz.

(1) In the twin-screw extruder, the respective screws influence each other so that the material is not rotated together with the screws and, hence, the compounding is not much influenced by characteristics of the material. Therefore, the twin-screw extruder is capable of processing an oil-rich or water-rich material which cannot be successfully processed by the single-screw extruder.

(2) Compared with the single-screw extruder, the twin-screw extruder is by far superior in shear force, compounding effect and transport capacity. Therefore, in the processing of a protein, for instance, the structurization of the protein which cannot be achieved with the single-screw extruder can be accomplished with the twin-screw extruder.

(3) The twin-screw extruder features a minimum heat of friction of the barrel and is, therefore, conducive to the ease of temperature control. As a consequence, the twin-screw extruder is more suited for pharmaceuticals which are vulnerable to high temperature.

The polymer to be used in the present invention can be virtually any natural or synthetic polymer that can be generally used as a raw material in the manufacture of pharmaceutical products and such that its functions are not adversely affected by the passage through the small die orifice or orifices of the twin-screw extruder.

Among such polymer are pH-dependent polymers, pH-independent polymers and water-soluble polymers, for instance, and specifically include the following.

Hydroxypropylmethylcellulose phthalate 220824 (HP50), hydroxypropylmethylcellulose phthalate 220731 (HP55), hydroxypropylmethylcellulose acetate succinate (AQOAT), carboxymethylethylcellulose (CMEC), cellulose acetate phthalate (CAP), methacrylic copolymer LD (L30 D55), methacrylic copolymer S (S-100), aminoalkyl methacrylate copolymer E (gastric coating base), poly(vinyl acetal) diethylaminoacetate (AEA), polyvinylpyrrolidone (K-25, 30, 90; PVP), ethylcellulose (EC), methacrylic copolymer RS (RS 30D), polyvinyl alcohol (PVA), methylcellulose (MC), hydroxypropylcellulose (HPC), hydroxypropylmethylcellulose 2208 (Metolose 90SH), hydroxypropylmethylcellulose 2906 (Metolose 65SH), hydroxypropylmethylcellulose 2910 (Metolose 60SH), carboxymethylcellulose sodium (sodium cellulose glycolate), dextrin, pullulan, Acacia, tragacanth, sodium alginate, propylene glycol alginate, agar powder, gelatin, starch, processed starch, phospholipids (lecithin), glucomannan and so on.

The polymers can be used independently or, if necessary, in a combination of two or more species.

The particle diameter of said polymer need not necessarily be finer that the size which can be fed from the hopper to the body of the twin-screw extruder and is generally not greater than 7000 μm and preferably not greater than 2000 μm. Coarser polymers can also be used by comminuting them beforehand.

The processing parameters such as pressure, temperature, feed rate of material, amounts and feed rates of water, plasticizer and other additives in the production process of the present invention are dependent on the type of drug and of polymer, the twin-extruder model used and other conditions but it is important to select a combination of parameters such that the drug, polymer, etc. will be maintained at temperatures below their decomposition points and vary the operating parameters according to the desired characteristics of the product.

The compounding ratio of the drug to the polymer should vary with the species of drug and of polymer, the objective, film characteristics and so on. Based on each part of the drug, the proportion of the polymer is generally 0.1 to 999 parts, preferably 0.5 to 500 parts and for still better results, 1 to 50 parts.

When the system contains a thermally labile drug and/or polymer, an aqueous solution or dispersion of a plasticizer may be added to the material prior to feeding to the twin-screw extruder or during compounding. Since this practice lowers the transition temperature of the polymer, the molding temperature setting can then be lower than the decomposition points of the drug and polymer to prevent thermal degradation of the drug and polymer. Of course, an aqueous plasticizer solution or dispersion may be added in the same manner when no heat-labile drug or polymer is contained in the system.

As the plasticizer which can be used for depressing the transition temperature of the polymer, those compounds which are generally used as plasticizers for film coating compositions in the pharmaceutical field can be mentioned. For example, the following compounds can be mentioned.

Cetanol, medium chain triglycerides, polyoxyethylene-polyoxypropylene glycol (Pluronic), macrogols (200, 300, 400, 600, 1000, 1500, 1540, 4000, 6000, 20000), triacetin, triethyl citrate (Citroflex), etc.

It should be understood that the plasticizer which can be used in the present invention is not limited to the species mentioned above but can be any compound having the property to lower the transition temperature of the polymer.

The level of addition of said plasticizer is dependent on the types of drug and polymer used but is appropriately 1 to 80% and preferably 5 to 50% relative to the polymer.

The method for addition of the plasticizer may be direct addition to the system containing the polymer and the drug before compounding or addition of an aqueous solution or dispersion of the plasticizer in the course of molding. There is no particular limitation on the method of addition.

The drug which can be used in the present invention is not particularly limited but is preferably a non-heat-labile drug, particularly a drug which is not decomposed at any temperature not exceeding 50° C. As such drugs, there can be mentioned the following, among others.

1. Antipyretic, analgesic and antiinflammatory agents

Indomethacin, aspirin, diclofenac sodium, ketoprofen, ibuprofen, mefenamic acid, dexamethasone, dexamethasone sodium sulfate, hydrocortisone, prednisolone, azulene, phenacetin, isopropylantipyrine, acetaminophen, benzydamine hydrochloride, phenylbutazone, flufenamic acid, sodium salicylate, choline salicylate, Sasapyrine (salsalate), clofezone, etodolac.

2. Antiulcer agents

Sulpiride, cetraxate hydrochloride, gefarnate, irsogladine maleate, cimetidine, ranitidine hydrochloride, famotidine, nizatidine, roxatidine acetate hydrochloride.

3. Coronary vasodilators

Nifedipine, isosorbide dinitrate, diltiazem hydrochloride, trapidil, dipyridamole, dilazep dihydrochloride, methyl 2,6-dimethyl-4 -(2-nitrophenyl)-5-(2-oxo-1,3,2-dioxaphosphorinan-2-yl) -1,4-dihydropyridine-3-carboxylate, verapamil, nicardipine, nicardipine hydrochloride, verapamil hydrochloride.

4. Peripheral vasodilators

Ifenprodil tartrate, cinepazide maleate, cyclandelate, cinnarizine, pentoxiphylline.

5. Antibiotics

Ampicillin, amoxicillin, cefalexin, erythromycin ethyl succinate, bacampicillin hydrochloride, minocycline hydrochloride, chloramphenicol, tetracycline, erythromycin.

6. Synthetic antimicrobial agents

Nalidixic acid, piromidic acid, pipemidic acid trihydrate, enoxacin, cinoxacin, ofloxacin, norfloxacin, ciprofloxacin hydrochloride, sulfamethoxazole-trimethoprim, 6-fluoro-1-methyl -7-[4-(5-methyl-2-oxo-1,3-dioxolen-4-yl)methyl-1-piperazinyl]-4 -oxo-4H[1,3]-thiazeto[3,2-a]quinoline-3-carboxylic acid.

7. Antispasmodic agents

Propantheline bromide, attopine sulfate, oxapium bromide, timepidium bromide, scopolamine butylbromide, trospium chloride, buttopium bromide, N-methylscopolamine methylsulfate, octatropine methylbromide.

8. Antitussive and antiasthmatic agents

Theophylline, aminophylline, methylephedrine hydrochloride, procaterol hydrochloride, trimethoquinol hydrochloride, codeine phosphate, cromoglicate sodium, tranilast, dextromethorphan hydrobromide, dimemorfan phosphate, clobutinol hydrochloride, fominoben hydrochloride, benproperine phosphate, tipepidine hibenzate, eprazinone hydrochloride, clofedanol hydrochloride, ephedrine hydrochloride, noscapine, carbetapentane citrate, oxeladin tannate, isoaminile citrate.

9. Bronchodilators

Diprophylline, salbutamol sulfate, clorprenaline hydrochloride, formoterol fumarate, orciprenaline sulfate, pirbuterol hydrochloride, hexoprenaline sulfate, bitolterol mesilate, clenbuterol hydrochloride, terbutaline sulfate, mabuterol hydrochloride, fenoterol hydrobromide, methoxyphenamine hydrochloride.

10. Diuretics

Furosemide, acetazolamide, trichlormethiazide, cyclothiazide, hydrochlorothiazide, hydroflumethiazide, ethiazide, cyclopentiazide, spironolactone, triamterene, chlorothiazide, piretanide, mefruside, etacrynic acid, azosemide, clofenamide.

11. Muscle relaxants

Chlorophenesin carbamate, tolperisone hydrochloride, eperisone hydrochloride, tizanidine hydrochloride, mephenesin, chlorzoxazone, phenprobamate, methocarbamol, chlormezanone, pridinol mesilate, afloqualone, baclofen, dantrolene sodium.

12. Cerebral metabolism improving agents

Meclofenoxate hydrochloride.

13. Minor tranquilizers

Oxazolam, diazepam, clotiazepam, medazepam, temazepam, fludiazepam, meprobamate, nitrazepam, chlordiazepoxide;

14. Major tranquilizers

Sulpiride, clocapramine hydrochloride, zotepine, chloropromazine, haloperidol.

15. β-Blockers

Pindolol, propranolol hydrochloride, carteolol hydrochloride, metoprolol tartrate, labetalol hydrochloride, oxprenolol hydrochloride, acebutolol hydrochloride, bufetolol hydrochloride, alprenolol hydrochloride, arotinolol hydrochloride, nadolol, bucumolol hydrochloride, indenolol hydrochloride, timolol maleare, befunolol hydrochloride.

16. Antiarrhythmic agents

Procainamide hydrochloride, disopyramide, aimaline, quinidine sulfate, aprindine hydrochloride, propafenone hydrochloride, mexiletine hydrochloride.

17. Antigout agents

Allopurinol, probenecid, colchicine, sulfinpyrazone, benzbromarone, bucolome.

18. Anticoagulants

Ticlopidine hydrochloride, dicoumarol, warlatin potassium.

19. Antiepileptics

Phenytoin, sodium valproate, metharbital, carhamazepine.

20. Antihistaminics

Chlorpheniramine maleate, clemastine fumarate, mequitazine, alimemazine tartrate, cyproheptadine hydrochloride.

21. Antiemetics

Difenidol hydrochloride, metoclopramide, domperidone, betahistine mesilate, trimebutine maleate.

22. Antihypertensive agents

Dimethylaminoethyl reserpilinate hydrochloride, rescinnamine, methyldopa, prazosin hydrochloride, bunazosin hydrochloride, clonidine hydrochloride, budralazine, urapidil.

23. Sympathomimetic agents

Dihydroergotamine mesilate, isoproterenol hydrochloride, etilefrine hydrochloride. p0 24. Expectorants Bromhexine hydrochloride, carbocysteine, cysteine ethyl ester hydrochloride, cysteine methyl ester hydrochloride.

25. Oral antidiabetic agents

Glibenclamide, tolbutamide, glymidine sodium.

26. Cardiovascular system drugs

Ubidecarenone, ATP 2Na.

27. Iron preparations

Ferrous sulfate, dried iron sulfate.

28. Vitamins

Vitamin $B_1$, vitamin $B_2$, vitamin $B_6$, vitamin $B_{12}$, vitamin C, folic acid.

29. Therapeutic agents for pollakiuria

Flavoxate hydrochloride, oxybutynin hydrochloride, terodiline hydrochloride, 4-diethylamino-1,1-dimethyl-2-butynyl (+)-α-cyclohexyl-α-phenylglycolate hydrochloride monohydrate.

30. Angiotensin converting enzyme inhibitors

Enalapril maleate, alacepril, delapril hydrochloride.

The solid dispersion prepared according to the invention can be easily comminuted using an appropriate mill or the like to provide a finely divided solid dispersion, which can be directly utilized as powders or granules. It can also be processed into a variety of dosage forms for oral administration, such as tablets, granules, fine granules, capsules, semi-solid dispersion-filled capsules, oily substance-filled capsules and so on.

In October 1991, a technology for the manufacture of a controlled release dosage form utilizing a single-screw extruder was disclosed (CapsuleNews, June/July, Vol. 1, No. 3, Warner-Lambert Co.).

However, the technology disclosed in the above literature is a process using a single-screw extruder which is by far inferior to the twin-screw extruder as pointed out hereinbefore and the product is also distinct from the solid dispersion provided by the process of the present invention. Furthermore, the above technology is intended for the manufacture of a slow release dosage form and this slow release dosage form is manufactured at high temperature.

Therefore, the above technology is irrelevant to the process of the invention which is intended for the manufacture of a solid dispersion overcoming the disadvantages of the prior art fusion and solvent processes.

EFFECTS OF INVENTION

In accordance with the present invention, a solid dispersion can be provided without exposing the drug and polymer to high temperature and without use of any organic solvent.

In accordance with the invention, a solid dispersion can be molded and taken out in a pure form and a solid dispersion of any desired size and shape can be manufactured by varying the discharge die orifice diameter and configuration.

Furthermore, other disadvantages of the fusion and solvent processes are successfully obviated.

BEST MODE OF PRACTICING THE INVENTION

The following examples, comparative Examples and Test Examples are intended to describe the present invention in further detail.

Example 1

Five-hundred (500) grams of Compound A (compound name: methyl 2,6-dimethyl-4-(2-nitrophenyl)-5-(2-oxo-1,3,2-dioxaphosphorinan -2-yl)-1,4-dihydropyridine-3-carboxylate; the same applies hereinafter) was pulverized and this bulk powder (mean particle diameter: 60 μm) was blended with 2500 g of hydroxypropylmethylcellulose acetate succinate (tradename: AQOAT, ASMF, Shin-etsu Chemical; the same applies hereinafter). Then, while a small quantity of water was added, the mixture was processed using a twin-screw extruder (KEX-30, Kurimoto Iron Works; the same applies hereinafter) equipped with a 4 mm φ×2-orifice die at a barrel temperature of 100° C. and an extrusion speed of 200 rpm to provide an extrudate (solid dispersion).

This extrudate was pulverized in a sample mill (Model AP-S, Hosokawa Iron Works; the same applies hereinafter) and the finely-divided powder thus obtained was used as samples for the release test (65–100 mesh), power X-ray diffraction analysis (250 mesh pass) and solubility (65–100 mesh).

Example 2

Five-hundred (500) grams of indomethacin was blended with 2500 g of hydroxypropylmethylcellulose phthalate (tradename: HPMCP, HP-55F grade, Shin-etsu Chemical; the same applies hereinafter), and while a 50% (w/w) aqueous solution of triethyl citrate was added, the composition was molded using a twin-screw extruder equipped with a 4 mm φ×2-orifice die at a barrel temperature of 80° C. and an extrusion speed of 200 rpm to provide an extrudate (solid dispersion).

This extrudate was comminuted in a sample mill and the resulting finely divided powder was used as samples for the release test, powder X-ray diffraction analysis and solubility.

Example 3

Five-hundred (500) grams of indomethacin was blended with 1500 g of poly(vinyl acetal) diethylaminoacetate (trademark: AEA, Sankyo Organic Chemicals) and while a 50% (w/w) aqueous solution of triacetin was added, the composition was molded using a twin-screw extruder equipped with a 4 mm φ×2-orifice die at a barrel temperature of 90° C. and an extrusion speed of 200 rpm to provide an extrudate (solid dispersion).

Example 4

Two-hundred (200) grams of Compound B (compound name: 4-diethylamino-1,1-dimethyl-2-butynyl (+)-α-cyclohexyl-α-phenylglycolate hydrochloride monohydrate) was blended with 1600 g of methacrylic copolymer LD (tradename: Budragit, grade b30D55, available from K. K. Higuchi Shokai) and 200 g of wheat starch. Then, while water was added (poured), the composition was molded using a twin-screw extruder equipped with a 4 mm φ×2-orifice die at a barrel temperature of 100° C. and an extrusion speed of 200 rpm to provide an extrudate (solid dispersion).

Example 5

Two-thousand (2000) grams of a 1:1 (w/w) mixture of indomethacin and ethyl cellulose (tradename: Ethocel, STD-45 type, Dow Chemical) was weighed out and wheat starch was added at the three levels of 300 g, 500 g and 1000 g. While a 5% (w/w) aqueous solution of triacetin was added at the rate of 5 ml/min., each of the above mixtures was molded using a twin-screw extruder equipped with 4 mm φ×2-orifice die at a barrel temperature of 80° C. and an extrusion speed of 200 rpm to provide an extrudate (solid dispersion). Each of these extrudates was pulverized in a sample mill and the resulting finely divided powder (65–100 mesh) was used as test samples.

Example 6

Three-hundred (300) grams of nifedipine was blended with 1500 g of hydroxypropylmethylcellulose acetate succinate and while water was added, the composition was molded using a twin-screw extruder equipped with 4 mm φ×2-orifice die at a barrel temperature of 100° C. and an extrusion speed of 200 rpm to provide an extrudate (solid dispersion).

This extrudate was pulverized in a sample mill and the resulting finely divided powder was used as samples for the release test (65–100 mesh), power X-ray diffraction analysis (250 mesh pass) and solubility (65–100 mesh).

Example 7

Two-hundred (200) grams of oxybutynin hydrochloride was blended with 1000 g of hydroxypropylmethylcellulose acetate succinate and while water was added, the composition was molded using a twin-screw extruder equipped with 2 mm φ×3-orifice die at a barrel temperature of 100° C. and an extrusion speed of 200 rpm to provide an extrudate (solid dispersion).

This extrudate was pulverized in a sample mill and the resulting finely divided powder was used as samples for the release test (65–100 mesh), power X-ray diffraction analysis (250 mesh pass) and solubility (65–100 mesh).

Example 8

Two-hundred (200) grams of nicardipine hydrochloride was blended with 1000 g of hydroxypropylmethylcellulose phthalate and while a 50% (w/w) aqueous solution of propylene glycol was added, the composition was molded using a twin-screw extruder equipped with 2 mm φ×3-orifice die at a barrel temperature of 80° C. and an extrusion speed of 200 rpm to provide an extrudate (solid dispersion).

This extrudate was pulverized in a sample mill and the resulting finely divided powder was used as samples for the release test (65–100 mesh), power X-ray diffraction analysis (250 mesh pass) and solubility (65–100 mesh).

Example 9

Five-hundred (500) grams of diclofenac sodium was blended with 2500 g of hydroxypropylmethylcellulose phthalate and while a 50% (w/w) aqueous solution of triethyl citrate was added, the composition was molded using a twin-screw extruder equipped with 4 mm φ×2-orifice die at a barrel temperature of 80° C. and an extrusion speed of 150 rpm to provide an extrudate (solid dispersion).

This extrudate was pulverized in a sample mill and the resulting finely divided powder was used as samples for the release test (65–100 mesh), power X-ray diffraction analysis (250 mesh pass) and solubility (65–100 mesh).

Comparative Example 1 Solvent Process

Five (5) grams of Compound A and 25 g of hydroxypropylmethylcellulose acetate succinate were weighed out and dissolved by addition of 700 ml of ethanol and 300 ml of methylene chloride. Then, using a rotary evaporator, the solvent was thoroughly evaporated at 50° C. to provide a solid (solid dispersion). This solid was pulverized in a table-top compact mill and the resulting fine powder was size-selected to provide comparative test samples for the release test (65–100 mesh), powder X-ray diffraction analysis (250 mesh pass) and solubility test (65–100 mesh).

Comparative Example 2

Five (5) grams of nifedipine and 25 g of hydroxypropylmethylcellulose acetate succinate were weighed out and dissolved by addition of 700 ml of ethanol and 300 ml of methylene chloride. Then, using a rotary evaporator, the solvent was thoroughly evaporated at 50° C. to provide a solid (solid dispersion). This solid was pulverized in a table-top compact mill and the resulting fine powder was size-selected to provide comparative test samples for the release test (65–100 mesh), powder X-ray diffraction analysis (250 mesh pass) and solubility test (65–100 mesh).

Comparative Example 3

Five (5) grams of oxybutynin hydrochloride and 25 g of hydroxypropylmethylcellulose acetate succinate were weighed out and dissolved by addition of 700 ml of ethanol and 300 ml of methylene chloride. Then, using a rotary evaporator, the solvent was thoroughly evaporated at 50° C. to provide a solid (solid dispersion). This solid was pulverized in a table-top compact mill and the resulting fine powder was size-selected to provide comparative test samples for the release test (65–100 mesh), powder X-ray diffraction analysis (250 mesh pass) and solubility test (65–100 mesh).

Comparative Example 4

Five (5) grams of nicardipine hydrochloride and 25 g of hydroxypropylmethylcellulose phthalate were weighed out and dissolved by addition of 700 ml of ethanol and 300 ml of methylene chloride. Then, using a rotary evaporator, the solvent was thoroughly evaporated at 50° C. to provide a solid (solid dispersion). This solid was pulverized in a table-top compact mill and the resulting fine powder was size-selected to provide comparative test samples for the release test (65–100 mesh), powder X-ray diffraction analysis (250 mesh pass) and solubility test (65–100 mesh).

Comparative Example 5

Five (5) grams of diclofenac sodium and 25 g of hydroxypropylmethylcellulose phthalate were weighed out and dissolved by addition of 700 ml of ethanol and 300 ml of methylene chloride. Then, using a rotary evaporator, the solvent was thoroughly evaporated at 50° C. to provide a solid (solid dispersion). This solid was pulverized in a table-top compact mill and the resulting fine powder was size-selected to provide comparative test samples for the release test (65–100 mesh) and powder X-ray diffraction analysis (250 mesh pass).

Test Example 1

The release test was carried out with the solid dispersions prepared in Example 1 (extruded product) and Comparative Example 1. As shown in FIG. 1, there was no release of Compound A under the conditions of JP Test Solution 1 (pH 1.2), 900 ml test solution and paddle speed 100 rpm. On the other hand, a quick release was obtained under the conditions of JP Test Solution 2 (pH 6.8), 900 ml test solution and paddle speed 100 rpm.

The above results indicated that the finely divided powder according to the process of the invention has the function of acting as an enteric coated product.

Test Example 2

The solid products obtained in Example 1 and Comparative Example 1 were subjected to powder X-ray diffraction analysis. As shown in FIG. 2, the results showed the disappearance of peaks of Compound A crystals which had been observed with the bulk powder and a 1:1 physical mixture.

Test Example 3

The solubility of the test sample prepared in Example 1 was determined. As shown in Table 1, there was found an approximately 4-fold increase in solubility as compared with the bulk substance. This solubility value approximated that of the solid dispersion prepared by the solvent process in Comparative Example 1.

TABLE 1

|  | Example 1 | Comparative Example 1 |
|---|---|---|
| Compounding ratio (Compound A:AQOAT) | 1:5 | 1:5 |
| Solubility of Compound A in solid dispersion (μ g/ml)(1) | 155 | 146 |
| Solubility of Compound A bulk substance (μ g/ml) (2) | 36.5 | 36.5 |
| Solubility ratio [(1)/(2)] | 4.2 | 4.0 |

TABLE 1-continued

|  | Example 1 | Comparative Example 1 |
|---|---|---|

Test method: Saturation dissolution method
Test conditions: Constant-temperature bath (25° C.)
Monocin (24-hr shaking, 24 cycles/min.)
JP Test Solution 2
Ultracentrifugation: 40000 rpm × 1 hr; the supernatant analyzed by HPLC.

The results of Test Examples 1, 2 and 3 indicate that the extrudate retains the fundamental properties of an enteric coated product and, yet, has been converted to a solid dispersion.

Test Example 4

The release test was carried out with the sample prepared in Example 2. As shown in FIG. 3, there was no release of indomethacin in JP Test Solution 1 (pH 1.2). On the other hand, a quick release was obtained in JP Test Solution 2 (pH 6.8).

The above results indicated that the finely divided powder according to the process of the invention has the function of acting as an enteric coated product.

Test Example 5

The sample obtained in Example 2 was subjected to powder X-ray diffraction analysis. As shown in FIG. 4, the results showed the disappearance of peaks of indomethacin crystals which had been observed with the bulk powder and a 1:1 physical mixture.

Test Example 6

The solubility of the solid dispersion prepared in Example 2 (extruded product) was determined. There was found an approximately 2-fold increase in solubility as compared with the bulk substance. This solubility value approximated that of the solid dispersion prepared by the solvent process.

Test Example 7

The 35 mg indomethacin equivalent of the sample obtained in Example 5 was weighed and added to 900 ml of JP Test Solution 1 (pH 1.2) and the release test was carried out at a paddle speed of 100 rpm using a measuring wavelength of 320 nm. The result shown in FIG. 5 indicates that the release of indomethacin was suppressed and that the rate of release increased with an increasing amount of wheat starch added.

Test Example 8

The release test was carried out with the solid dispersions prepared in Example 6 and Comparative Example 2. As shown in FIG. 6, there was no release of nifedipine in JP Test Solution 1 (pH 1.2). On the other hand, a quick release was obtained in JP Test Solution 2 (pH 6.8).

The above results indicated that the finely divided powder according to the process of the invention has the function of acting as an enteric coated product.

Test Example 9

The solid products obtained in Example 6 and Comparative Example 2 were subjected to powder X-ray diffraction analysis. As shown in FIG. 7, the results showed the disappearance of peaks of nifedipine crystals which had been observed with the bulk powder and a 1:1 physical mixture.

Test Example 10

The solubility of the solid products prepared in Example 6 and Comparative Example 2 was determined. As shown in Table 2, there was found an approximately 5-fold increase in solubility as compared with the bulk substance. This solubility value was close to that of the solid dispersion prepared by the solvent process in Comparative Example 2.

TABLE 2

|  | Example 6 | Comparative Example 2 |
|---|---|---|
| Compounding ratio (Nifedipine:AQOAT) | 1:5 | 1:5 |
| Solubility of nifedipine in solid dispersion (μ g/ml)(1) | 26.3 | 28.6 |
| Solubility of nifedipine bulk substance (μ g/ml) (2) | 5.6 | 5.6 |
| Solubility ratio [(1)/(2)] | 4.7 | 5.1 |

Test method: Saturation dissolution method
Test conditions: Constant-temperature bath (25° C.)
Monocin (24-hr shaking, 24 cycles/min.)
JP Test Solution 2
Ultracentrifugation: 40000 rpm × 1 hr; the supernatant analyzed by HPLC.

The results of Test Examples 8, 9 and 10 indicate that the extrudate containing nifedipine retains the fundamental properties of an enteric coated product and, yet, has been converted to a solid dispersion.

Test Example 11

The release test was carried out with the solid dispersions prepared in Example 7 and Comparative Example 3. As shown in FIG. 8, there was no release of oxybutynin hydrochloride in JP Test Solution 1 (pH 1.2). On the other hand, a quick release was obtained in JP Test Solution 2 (pH 6.8).

The above results indicated that the finely divided powder provided by the process of the invention has the function of acting as an enteric coated product.

Test Example 12

The solid dispersions obtained in Example 7 and Comparative Example 3 were subjected to powder X-ray diffraction analysis. As shown in FIG. 9, the patterns showed the disappearance of peaks of oxybutynin hydrochloride crystals which had been observed with the bulk powder and a 1:1 physical mixture.

Test Example 13

The solubility of the solid dispersions prepared in Example 7 and Comparative Example 3 were determined. As shown in Table 3, there was found an approximately 3-fold increase in solubility as compared with the bulk substance. This solubility value approximated that of the solid dispersion prepared by the solvent process in Comparative Example 3.

TABLE 3

|  | Example 7 | Comparative Example 3 |
|---|---|---|
| Compounding ratio (oxybutynin hydrochloride:AQOAT) | 1:5 | 1:5 |
| Solubility of oxybutynin hydrochloride in solid dispersion (μ g/ml)(1) | 473.4 | 490.1 |
| Solubility of oxybutynin hydrochloride bulk substance (μ g/ml) (2) | 162.5 | 162.5 |
| Solubility ratio [(1)/(2)] | 2.9 | 3.0 |

Test method: Saturation dissolution method
Test conditions: Constant-temperature bath (25° C.)
Monocin (24-hr shaking, 24 cycles/min.)
JP Test Solution 2
Ultracentrifugation: 40000 rpm × 1 hr; the supernatant analyzed by HPLC.

The results of Test Examples 11, 12 and 13 indicate that the extrudate containing oxybutynin hydrochloride retains the fundamental properties of an enteric coated product and, yet, has been converted to a solid dispersion.

Test Example 14

The release test was carried out with the solid dispersions prepared in Example 8 and Comparative Example 4. As shown in FIG. 10, there was no release of nicardipine hydrochloride in JP Test Solution 1 (pH 1.2). On the other hand, a quick release was obtained in JP Test Solution 2 (pH 6.8).

The above results indicated that the finely divided powder according to the process of the invention has the function of acting as an enteric coated product.

Test Example 15

The solid dispersions obtained in Example 8 and Comparative Example 4 were subjected to powder X-ray diffraction analysis. As shown in FIG. 11, the patterns showed the disappearance of peaks of nicardipine hydrochloride crystals which had been observed with the bulk powder and a 1:1 physical mixture.

Test Example 16

The solubility of the solid dispersions prepared in Example 8 and Comparative Example 4 were determined. As shown in Table 4, there was found an approximately 6-fold increase in solubility as compared with the bulk substance. This solubility value approximated that of the solid dispersion prepared by the solvent process in Comparative Example 4.

TABLE 4

|  | Example 8 | Comparative Example 4 |
|---|---|---|
| Compounding ratio (nicardipine hydrochloride:AQOAT) | 1:5 | 1:5 |
| Solubility of nicardipine hydrochloride in solid dispersion (μ g/ml)(1) | 52.6 | 47.6 |
| Solubility of nicardipine hydrochloride bulk substance (μ g/ml) (2) | 8.5 | 8.5 |
| Solubility ratio [(1)/(2)] | 6.2 | 5.6 |

TABLE 4-continued

|  | Example 8 | Comparative Example 4 |
|---|---|---|

Test method: Saturation dissolution method
Test conditions: Constant-temperature bath (25° C.)
Monocin (24-hr shaking, 24 cycles/min.)
JP Test Solution 2
Ultracentrifugation: 40000 rpm × 1 hr; the supernatant analyzed by HPLC.

The results of Test Examples 14, 15 and 16 indicate that the extrudate containing nicardipine hydrochloride retains the fundamental properties of an enteric coated product and, yet, has been converted to a solid dispersion.

Test Example 17

The release test was carried out with the solid dispersions prepared in Example 9 and Comparative Example 5. As shown in FIG. 12, there was no release of diclofenac sodium in JP Test Solution 1 (pH 1.2). On the other hand, a quick release was obtained in JP Test Solution 2 (pH 6.8).

The above results indicated that the finely divided powder according to the process of the invention has the function of acting as an enteric coated product.

Test Example 18

The solid products obtained in Example 9 and Comparative Example 5 were subjected to powder X-ray diffraction analysis. As shown in FIG. 13, the patterns showed the disappearance of peaks of diclofenac sodium crystals which had been observed with the bulk powder and a 1:1 physical mixture.

The results of Test Examples 17 and 18 indicate that the extrudate containing diclofenac sodium retains the fundamental properties of an enteric coated product and, yet, has been converted to a solid dispersion.

Figure 1:
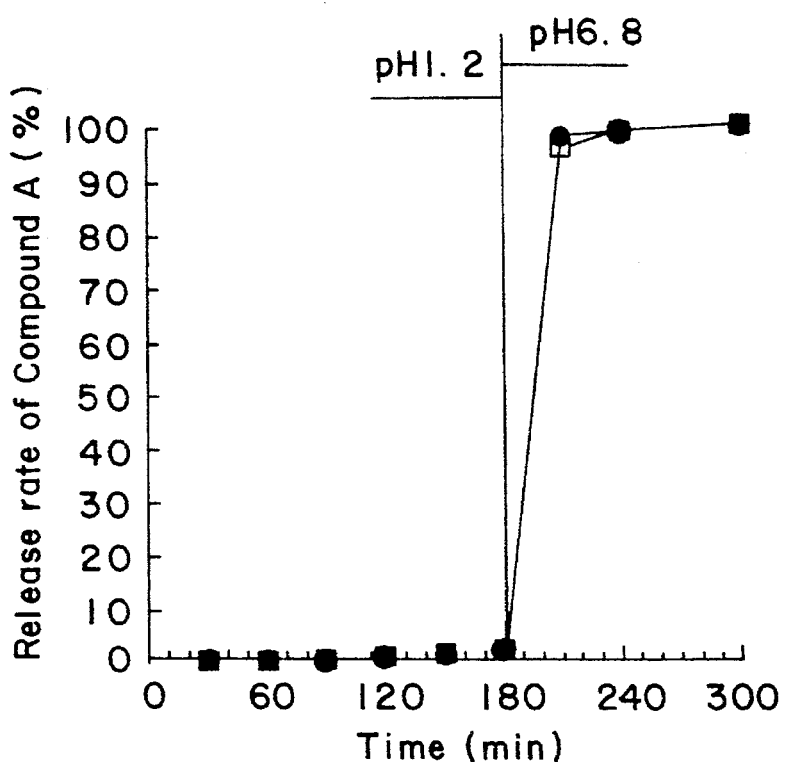
FIG. 1 shows the results of a release test with solid dispersions. The curve up to 180 minutes following the beginning of the test represents the result generated with JP Test Solution 1 (pH 1.2) and the curve after 180 minutes following the beginning of the test represents the result obtained with JP Test Solution 2 (pH 6.8). The time (in minutes) is plotted on the abscissa and the release rate (%) of Compound A is plotted on the ordinate. In the figure, ● represents the release curve of the solid dispersion obtained in Example 1 and □ represents the release curve of the solid dispersion obtained in Comparative Example 1.
Figure 2:
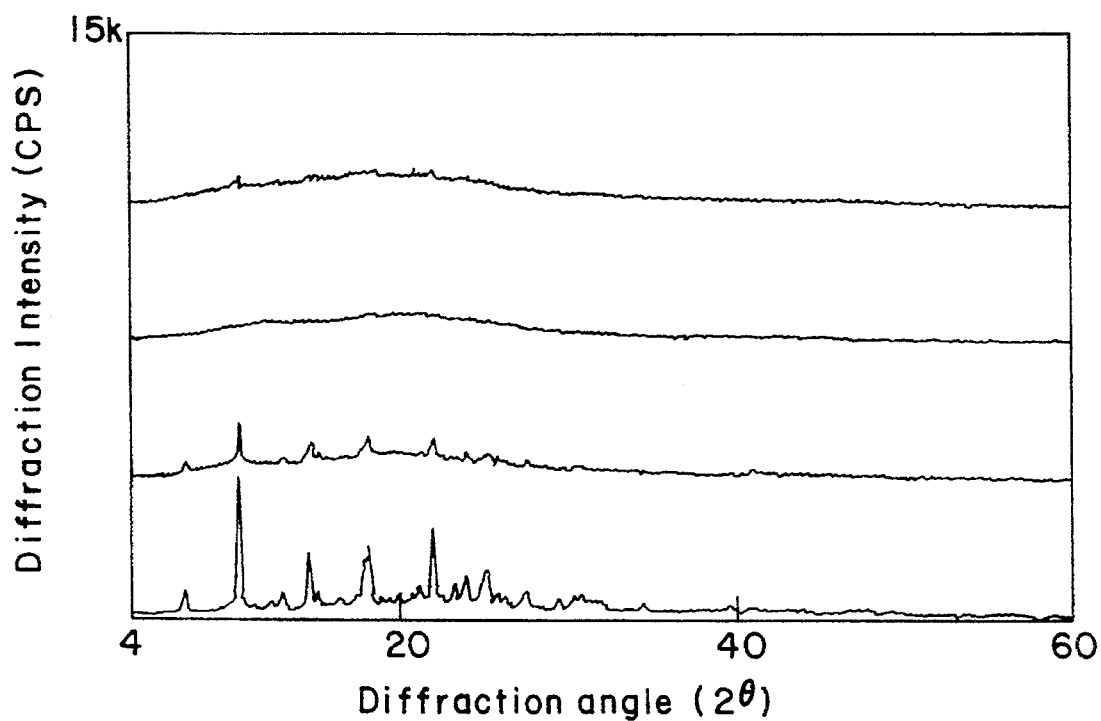
FIG. 2 shows the results of powder X-ray diffraction analysis of Compound A-containing solid dispersions. The uppermost powder X-ray diffraction pattern represents the X-ray diffraction pattern of the solid dispersion obtained in Example 1; the second powder X-ray diffraction pattern as reckoned from the top is the X-ray diffraction pattern of the solid dispersion obtained in Comparative Example 1; the third powder X-ray diffraction pattern as reckoned from the top is the X-ray diffraction pattern of a physical 1:5 mixture of Compound A and hydroxypropylmethylcellulose acetate succinate (AQOAT, AS-MF grade) (Compound A:AQOAT= the same as used in Example 1 and Comparative Example 1); and the downmost powder X-ray diffraction pattern is the X-ray diffraction pattern of Compound A bulk substance. The diffraction angle (2 θ) is plotted on the abscissa and the diffraction intensity (CPS) on the ordinate.
Figure 3:
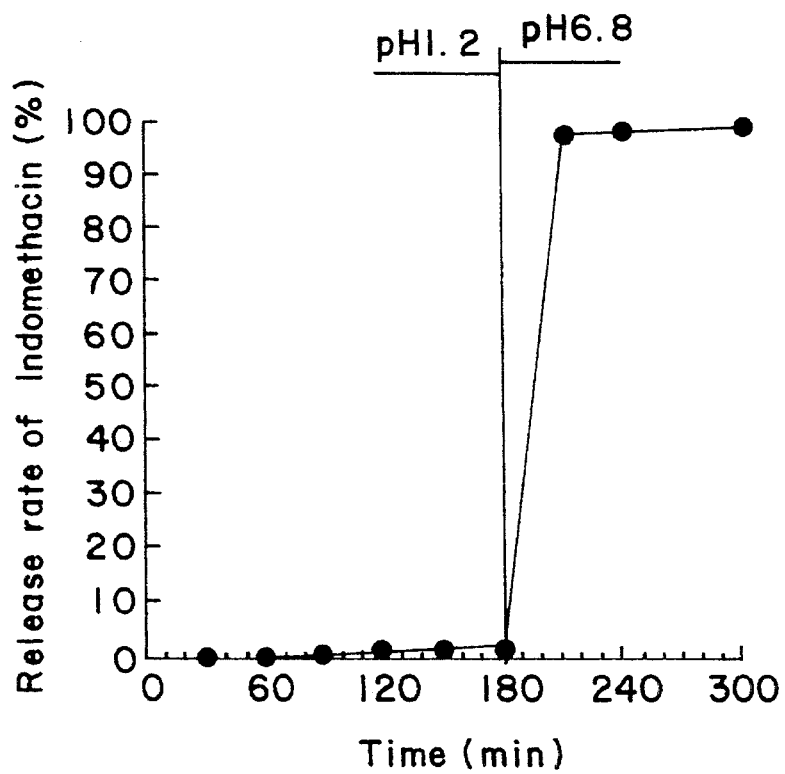
FIG. 3 shows the results of a release test with indomethacin-containing solid dispersions prepared in Example 2. The time (in minutes) is plotted on the abscissa and the release rate (%) of indomethacin is plotted on the ordinate.
Figure 4:
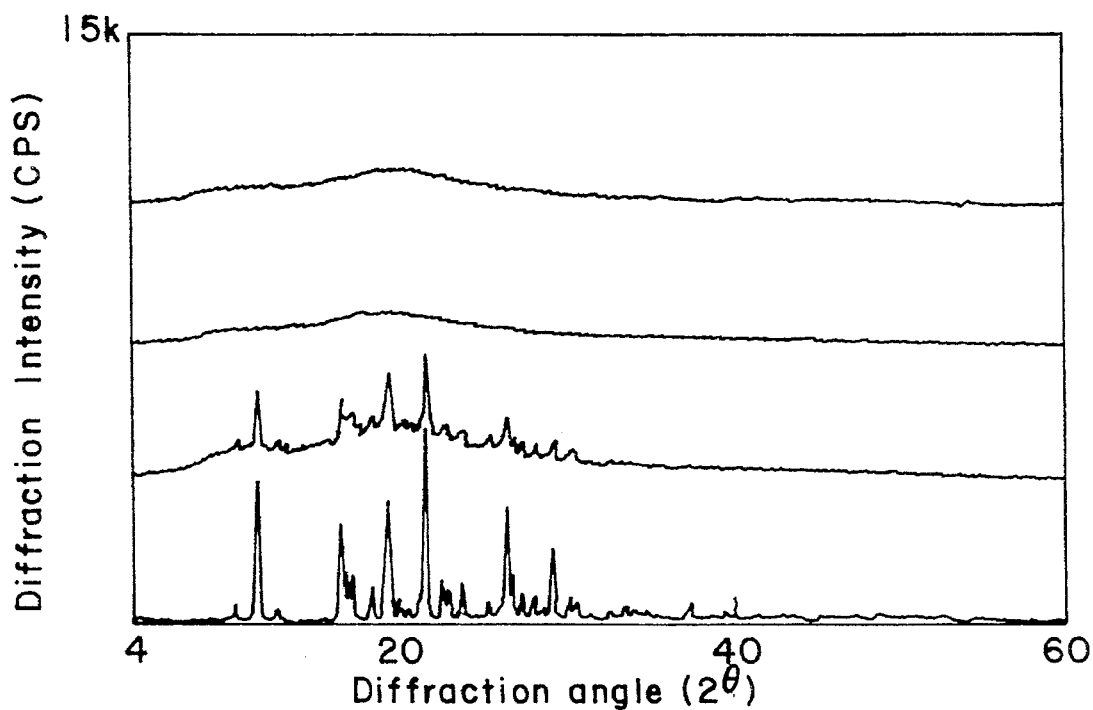
FIG. 4 shows the results of powder X-ray diffraction analysis of indomethacin-containing solid dispersions. The uppermost powder X-ray diffraction pattern represents the X-ray diffraction pattern of the solid dispersion obtained in Example 2; the second powder X-ray diffraction pattern as reckoned from the top is the X-ray diffraction pattern of a 1:5 solid dispersion of indomethacin and hydroxypropylmethylcellulose phthalate (HPMCP, HP-55F grade) (indomethacin:HPMCP=the same as used in Example 2) prepared by the so-called solvent process; the third powder X-ray diffraction pattern as reckoned from the top is the X-ray diffraction pattern of a physical 1:5 mixture of indomethacin and HPMCP (indomethacin:HPMEP=the same as used in Example 2); and the downmost powder X-ray diffraction pattern is the diffraction pattern of indomethacin bulk substance. The diffraction angle (2 θ) is plotted on the abscissa and the diffraction intensity (CPS) on the ordinate.
Figure 5:
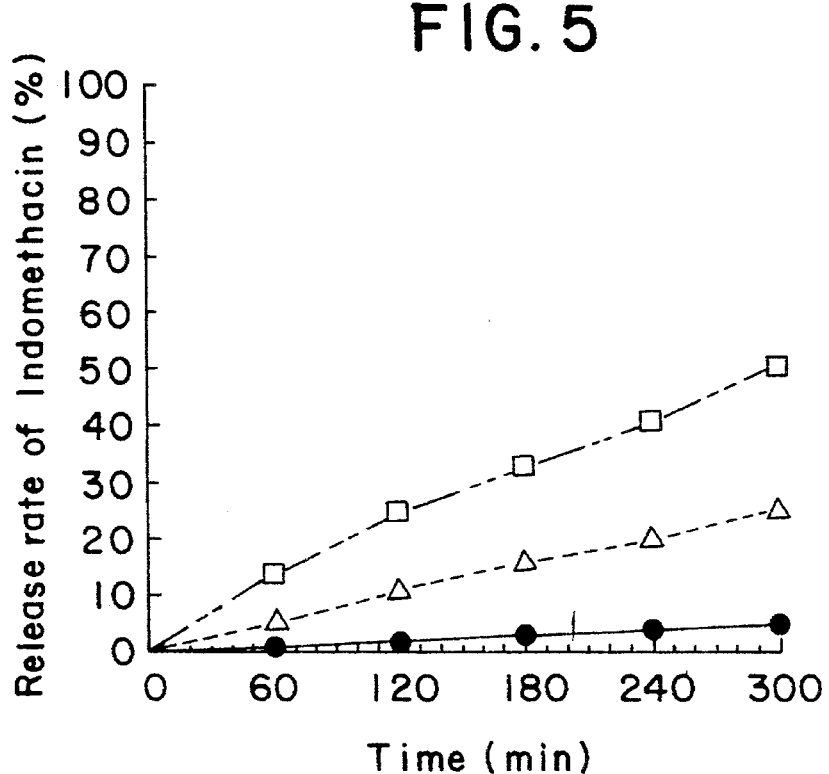
FIG. 5 shows the results of a release test with indomethacin-containing solid dispersions prepared in Example 5 in JP Test Solution 1 (pH 1.2). The time (in minutes) is plotted on the abscissa and the release rate (%) of indomethacin is plotted on the ordinate. In the figure, ● represents the release curve of the solid dispersion obtained by addition of 300 g of wheat starch in Example 5, △ represents the release curve of the solid dispersion obtained by addition of 500 g of wheat starch in Example 5 and □ represents the release curve of the solid dispersion obtained by addition of 1000 g of wheat starch in Example 5.
Figure 6:
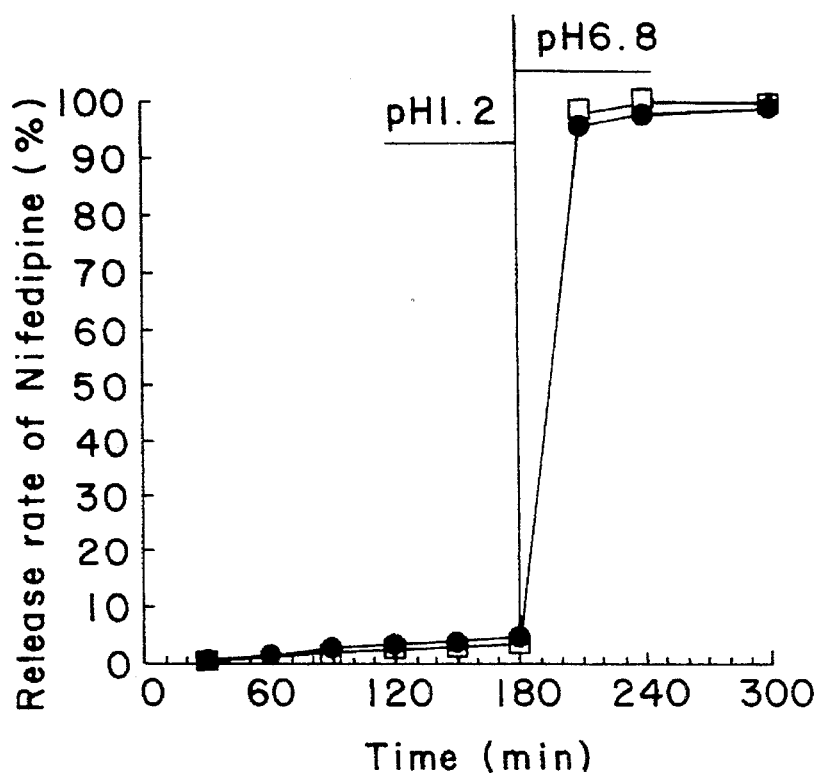
FIG. 6 shows the results of a release test with nifedipine-containing solid dispersions prepared in Example 6 and Comparative Example 2. The time (in minutes) is plotted on the abscissa and the release rate (%) of nifedipine is plotted on the ordinate. In the figure, ● represents the release curve of the solid dispersion obtained in Example 6 and □ represents the release curve of the solid dispersion obtained in Comparative Example 2.
Figure 7:
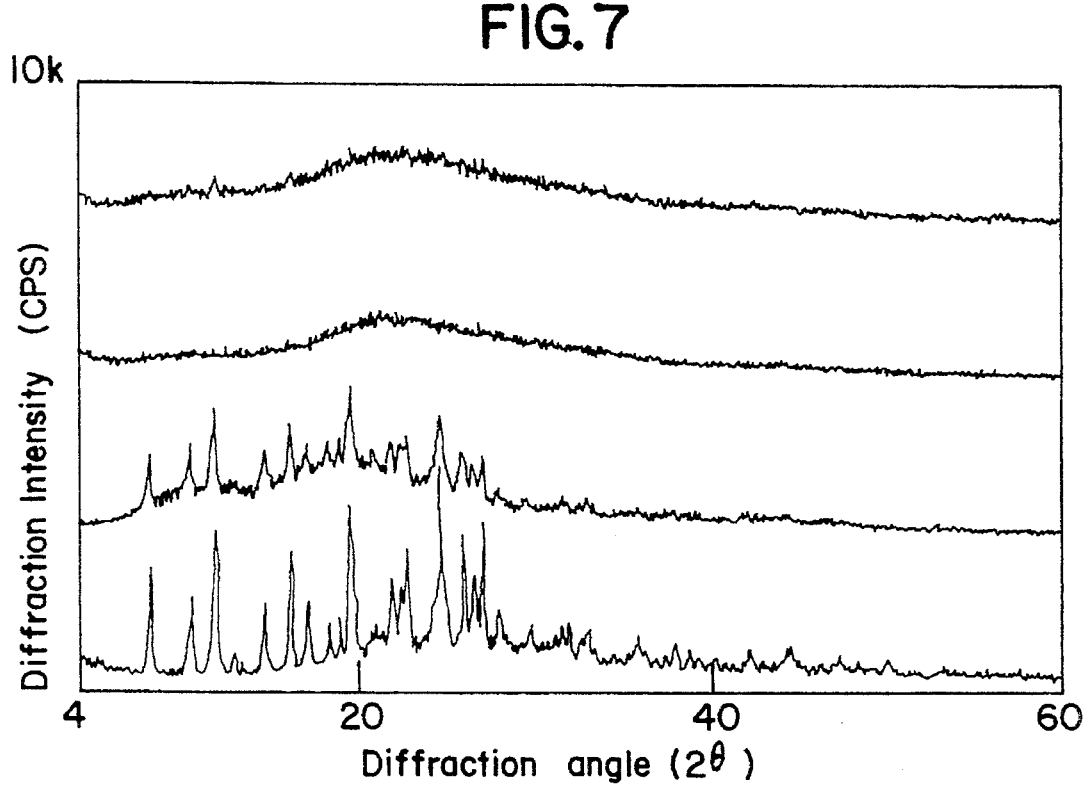
FIG. 7 shows the results of powder X-ray diffraction analysis of nifedipine-containing solid dispersions. The uppermost powder X-ray diffraction pattern represents the X-ray diffraction pattern of the solid dispersion obtained in Example 6; the second powder X-ray diffraction pattern as reckoned from the top is the X-ray diffraction pattern of the solid dispersion obtained in Comparative Example 2; the third powder X-ray diffraction pattern as reckoned from the top is the X-ray diffraction pattern of a physical 1:5 mixture of nifedipine and hydroxypropylmethylcellulose acetate succinate (AQOAT, AS-MF grade) (nifedipine:AQOAT=the same as used in Example 6 and Comparative Example 2); and the downmost powder X-ray diffraction pattern is the X-ray diffraction pattern of nifedipine bulk substance. The diffraction angle (2 θ ) is plotted on the abscissa and the diffraction intensity (CPS) on the ordinate.
Figure 8:
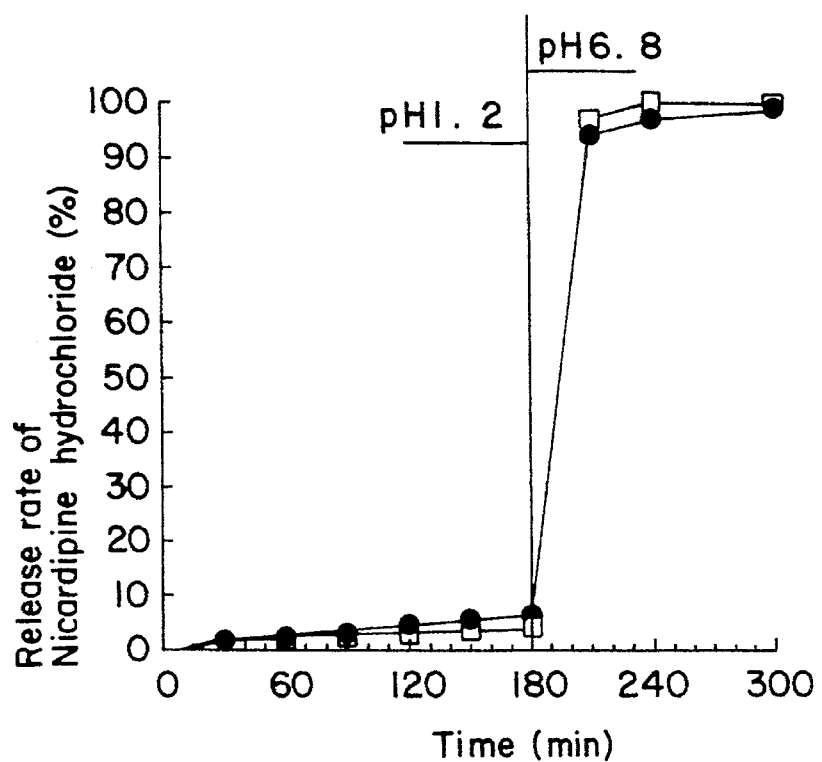
FIG. 8 shows the results of a release test with oxybutynin hydrochloride-containing solid dispersions prepared in Example 7 and Comparative Example 3. The time (in minutes) is plotted on the abscissa and the release rate (%) of oxybutynin hydrochloride is plotted on the ordinate. In the figure, ● represents the release curve of the solid dispersion obtained in Example 7 and ● represents the release curve of the solid dispersion obtained in Comparative Example 3.
Figure 9:
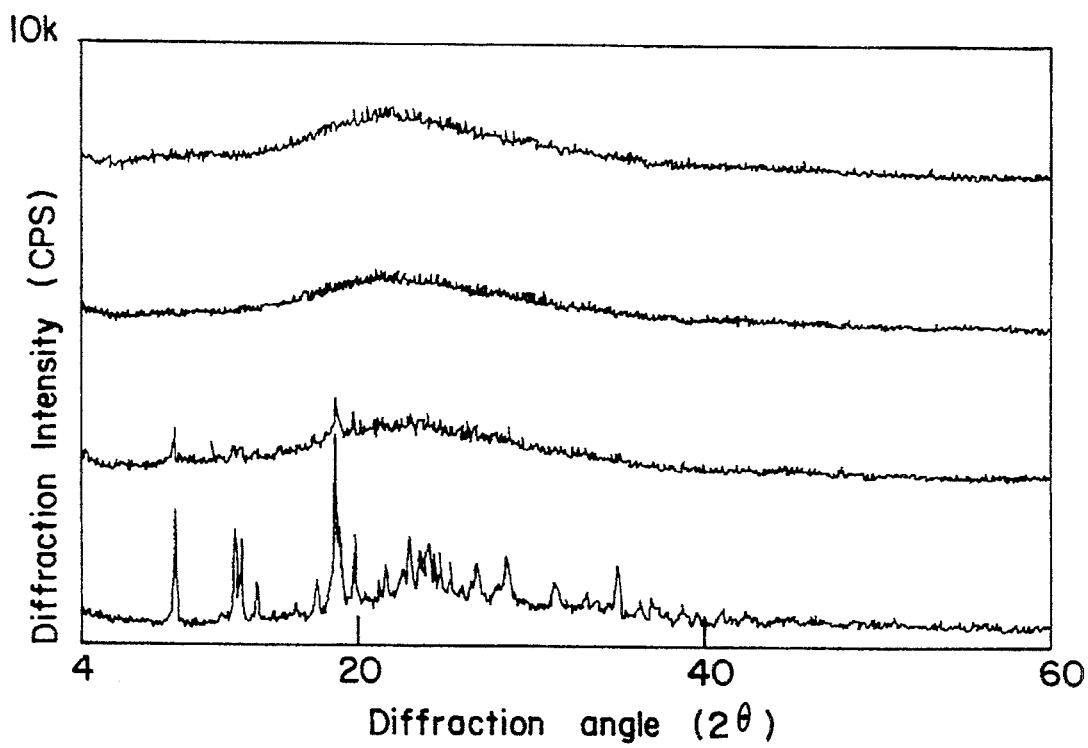
FIG. 9 shows the results of powder X-ray diffraction analysis of oxybutynin hydrochloride-containing solid dispersions. The uppermost powder X-ray diffraction pattern represents the X-ray diffraction pattern of the solid dispersion obtained in Example 7; the second powder X-ray diffraction pattern as reckoned from the top is the X-ray diffraction pattern of the solid dispersion obtained in Comparative Example 3; the third powder X-ray diffraction pattern as reckoned from the top is the X-ray diffraction pattern of a physical 1:5 mixture of oxybutynin hydrochloride and hydroxypropylmethylcellulose acetate succinate (AQOAT, AS-MF grade) (oxybutynin hydrochloride:AQOAT=the same as used in Example 7 and Comparative Example 3); and the downmost powder X-ray diffraction pattern is the X-ray diffraction pattern of oxybutynin hydrochloride bulk substance. The diffraction angle (2 θ) is plotted on the abscissa and the diffraction intensity (CPS) on the ordinate.
Figure 10:
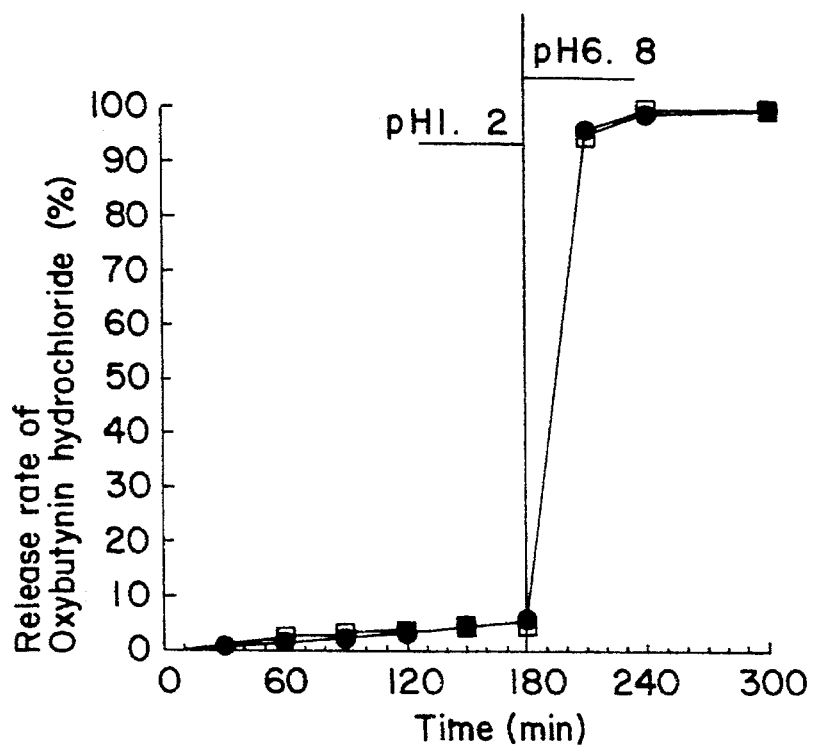
FIG. 10 shows the results of a release test with nicardipine hydrochloride-containing solid dispersions prepared in Example 8 and Comparative Example 4. The time (in minutes) is plotted on the abscissa and the release rate (%) of nicardipine hydrochloride is plotted on the ordinate. In the figure, ● represents the release curve of the solid dispersion obtained in Example 8 and □ represents the release curve of the solid dispersion obtained in Comparative Example 4.
Figure 11:
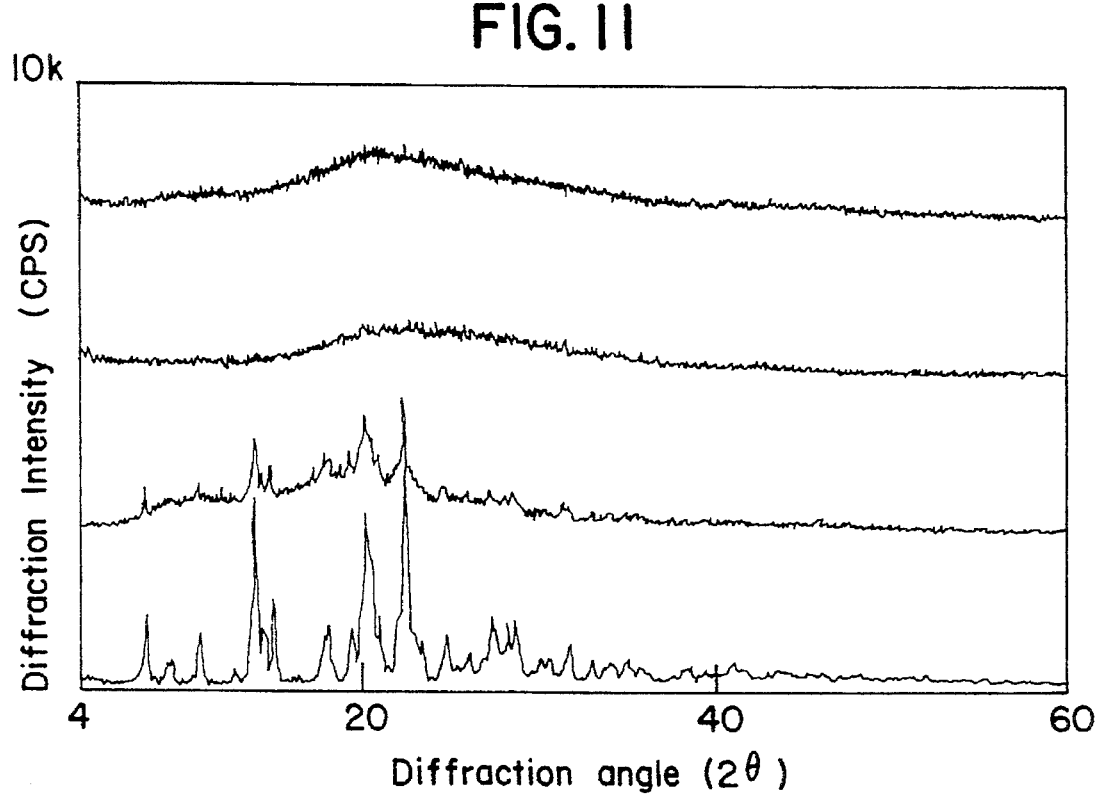
FIG. 11 shows the results of powder X-ray diffraction analysis of nicardipine hydrochloride-containing solid dispersions. The uppermost powder X-ray diffraction pattern represents the X-ray diffraction pattern of the solid dispersion obtained in Example 8; the second powder X-ray diffraction pattern as reckoned from the top is the X-ray diffraction pattern of the solid dispersion obtained in Comparative Example 4; the third powder X-ray diffraction pattern as reckoned from the top is the X-ray diffraction pattern of a physical 1:5 mixture of nicardipine hydrochloride and hydroxypropylmethylcellulose phthalate (HPMCP, HP-55F grade) (nicardipine hydrochloride:HPMCP=the same as used in Example 8 and Comparative Example 4); and the downmost powder X-ray diffraction pattern is the X-ray diffraction pattern of nicardipine hydrochloride bulk substance. The diffraction angle (2 θ) is plotted on the abscissa and the diffraction intensity (CPS) on the ordinate.
Figure 12:
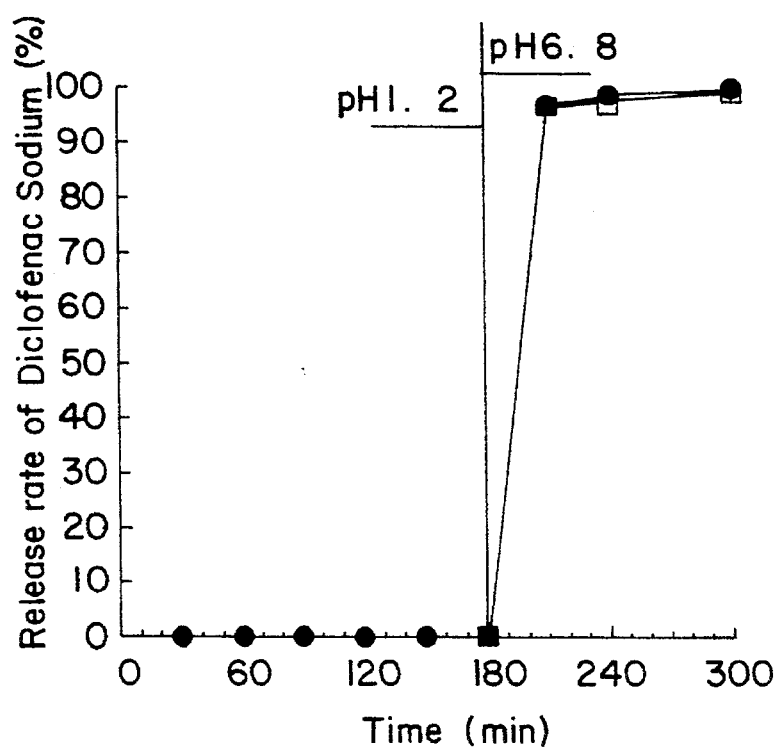
FIG. 12 shows the results of a release test with diclofenac sodium-containing solid dispersions prepared in Example 9 and Comparative Example 5. The time (in minutes) is plotted on the abscissa and the release rate (%) of diclofenac sodium is plotted on the ordinate. In the figure, ● represents the release curve of the solid dispersion obtained in Example 9 and □ represents the release curve of the solid dispersion obtained in Comparative Example 5.
Figure 13:
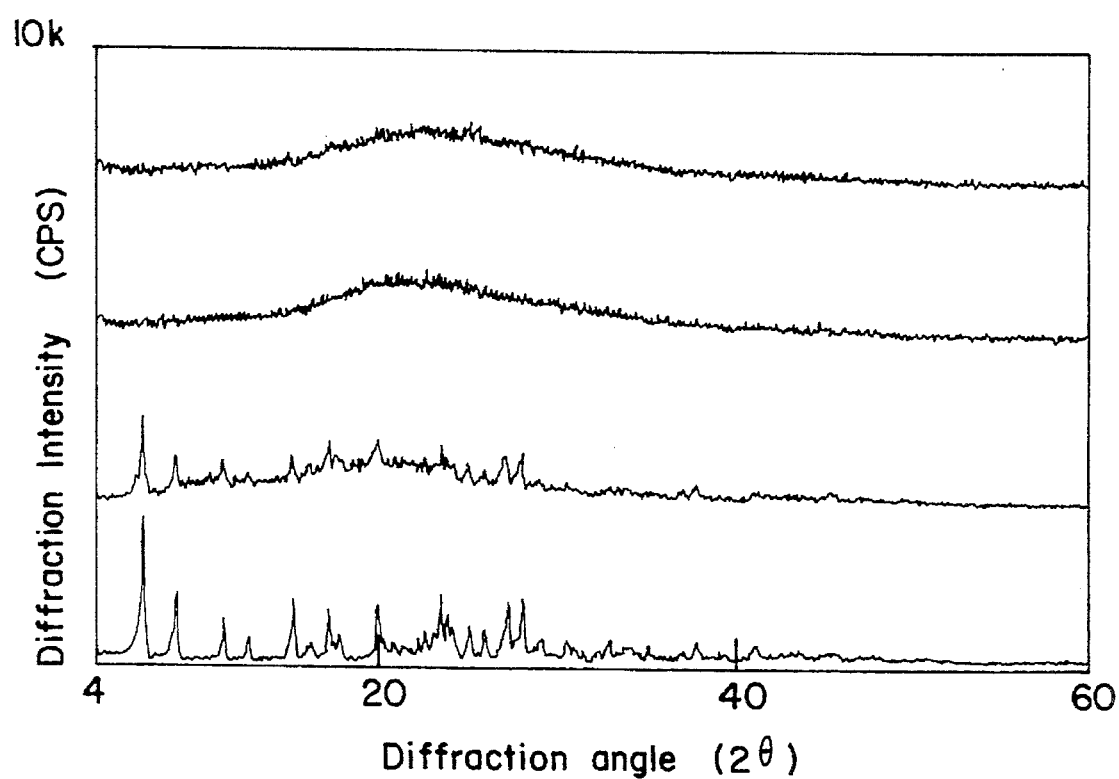
FIG. 13 shows the results of powder X-ray diffraction analysis of diclofenac sodium-containing solid dispersions. The uppermost powder X-ray diffraction pattern represents the X-ray diffraction pattern of the solid dispersion obtained in Example 9; the second powder X-ray diffraction pattern as reckoned from the top is the X-ray diffraction pattern of the solid dispersion obtained in Comparative Example 5; the third powder X-ray diffraction pattern as reckoned from the top is the X-ray diffraction pattern of a physical 1:5 mixture of diclofenac sodium and hydroxypropylmethylcellulose phthalate (HPMCP, HP-55F grade) (diclofenac sodium:HPMCP=the same as used in Example 9 and Comparative Example 5); and the downmost powder X-ray diffraction pattern is the X-ray diffraction pattern of diclofenac sodium bulk substance. The diffraction angle (2 θ) is plotted on the abscissa and the diffraction intensity (CPS) on the ordinate.

We claim:

1. A process for producing a solid dispersion of a drug dissolved or dispersed in a polymer carrier or diluent which comprises passing a mixture comprising said drug and said polymer through a twin screw compounding extruder having retaining barrels, with said twin screw compounding extruder being equipped with paddle means on each of two screw shafts, whereby said mixture passes between said paddle means and is sheared and compounded thereby, and operating said twin screw extruder while sufficiently heating the barrels to obtain an extrudate in the form of said solid dispersion and wherein said heating is to a temperature below the decomposition temperature of the drug or polymer.

2. A process according to claim 1 where said drug is selected from the group consisting of antipyretic agents, analgesic agents, antiinflammatory agents, antiulcer agents, coronary vasodilators, peripheral vasodilators, antibiotics, synthetic antimicrobial agents, antispasmodic agents, antitussive and antiasthmatic agents, bronchodilators, diuretics, muscle relaxants, cerebral metabolism improving agents, minor tranquilizers, major tranquilizers, β-blockers, antiarrhythmic agents, antigout agents, anticoagulants, antiepileptics, antihistaminics, antiemetics, antihypertensive agents, sympathomimetic agents, expectorants, oral antidiabetic agents, cardiovascular system drugs, iron preparations, vitamins, therapeutic agents for pollakiuria, and angiotensin-converting enzyme inhibitors.

3. A process according to claim 1 wherein said polymer is any natural or synthetic polymer which is capable of being employed as a raw material in the manufacture of pharmaceutical wherein said polymer's functions are not adversely affected by passage through the twin-screw extruder.

4. A process according to claim 3 wherein said polymer is a pH-dependent polymer, a pH-independent polymer or a water-soluble polymer.

5. A process according to claim 4 wherein said process employs a combination of two or more species of said polymer.

6. A process according to claim 1 wherein said polymer has a particle diameter of not greater than 7,000 μm.

7. A process according to claim 1 wherein said polymer has a particle diameter of not greater than 2,000 μm.

8. A process according to claim 1 wherein said drug is not decomposed at any temperature below 50° C. and is a thermally labile drug or said polymer is a thermally labile polymer and another component of the solid dispersion is an aqueous solution or dispersion of a plasticizer.

9. A process according to claim 8 wherein said plasticizer is selected from the group consisting of cetanol, medium chain triglycerides, polyoxyethylenepolyoxypropylene glycol, and macrogols (200, 300, 400, 600, 1,000, 1,500, 1,540, 4,000, 6,000, 20,000).

10. A process according to claim 4 wherein said polymer is selected from the group consisting of hydroxypropylmethylcellulose phthalate, hydroxypropylmethylcellulose acetate succinate, carboxymethylethylcellulose, cellulose acetate phthalate, methacrylic acid copolymer LD, methacrylic acid copolymer S, aminoalkyl methacrylate copolymer E, poly (vinyl acetal) diethylaminoacetate, polyvinyl pyrrolidone, ethylcellulose, methacrylic acid copolymer RS, polyvinyl alcohol, methylcellulose, hydroxypropylcellulose, hydroxypropylmethylcellulose, carboxymethylcellulose sodium, dextrin, pullulan, acacia, tragacanth, sodium alginate, propylene glycol alginate, agar powder, gelatin, starch, processed starch and glucomannan.

11. A process according to claim 1 wherein the passing step is performed while water, or an aqueous solution or dispersion of a plasticizer is added into the barrel.

12. A process according to claim 1 wherein the temperature of each barrel is in the range from 50° C. up to a temperature at which neither the drug nor the polymer decomposes.

* * * * *